United States Patent [19]

Stephenson et al.

[11] Patent Number: 5,211,678
[45] Date of Patent: May 18, 1993

[54] APPARATUS, METHOD AND SYSTEM FOR MONITORING FLUID

[75] Inventors: Stanley V. Stephenson; Ronald E. Dant; Robert L. Toellner; Edward P. Arnold; Thuong Van Le; Leslie N. Berryman, all of Duncan, Okla.

[73] Assignee: Halliburton Company, Duncan, Okla.

[21] Appl. No.: 744,776

[22] Filed: Aug. 14, 1991

[51] Int. Cl.$^5$ .................. G01F 23/14; G01N 9/26
[52] U.S. Cl. .................. 73/149; 73/32 R; 73/300; 73/301; 73/438
[58] Field of Search ............ 73/32 A, 32 R, 298–303, 73/149, 438, 439

[56] References Cited

U.S. PATENT DOCUMENTS

| | | | |
|---|---|---|---|
| 1,289,755 | 12/1918 | Haynes | 73/300 |
| 2,389,241 | 11/1945 | Silverman | 340/854.5 |
| 3,900,878 | 8/1975 | Tsao | 340/854.5 |
| 4,252,097 | 2/1981 | Hartford et al. | 73/32 R |
| 4,425,787 | 1/1984 | Saraf | 73/32 R |
| 4,630,478 | 12/1986 | Johnson | 73/299 |
| 4,669,309 | 6/1987 | Cornelius | 73/299 |
| 5,052,222 | 10/1991 | Stoepfel | 73/299 |
| 5,146,783 | 9/1992 | Jansche et al. | 73/301 |

OTHER PUBLICATIONS

Halliburton Services brochure entitled "ARC System (Automated Remoted Control)"–published more than one year prior to Aug., 1991.

Primary Examiner—Hezron E. Williams
Assistant Examiner—George M. Dombroske
Attorney, Agent, or Firm—Stephen R. Christian; E. Harrison Gilbert, III

[57] ABSTRACT

Fluid level in a container is determined using a single pressure transducer connected to a portable body. The body contains a computer having a memory in which fluid level-to-fluid volume conversion data are stored for different shapes of containers so that fluid volume can be readily obtained for the shape of the respective container once fluid level is determined. These features allow a single monitoring apparatus to be used for monitoring different types of containers. The apparatus preferably includes a radio so that multiple apparatus can communicate in a system with a central remote operator interface device. Fluid level is determined by dividing a pressure reading from the bottom of the fluid by a fluid density determined from two prior pressure reading taken across a known distance (density equals the difference between the two readings divided by the distance).

10 Claims, 14 Drawing Sheets

Microfiche Appendix Included
(209 Microfiche, 3 Pages)

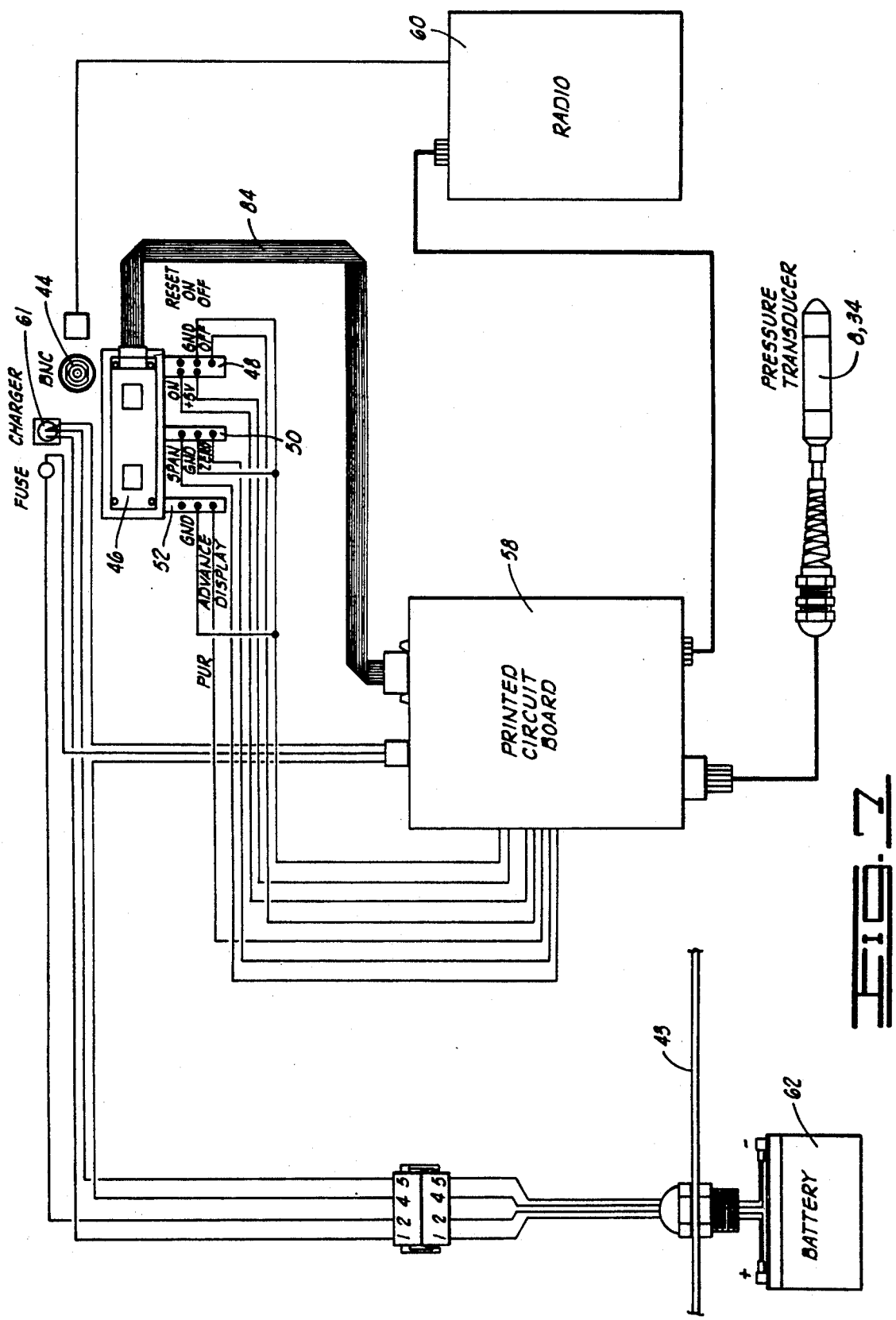

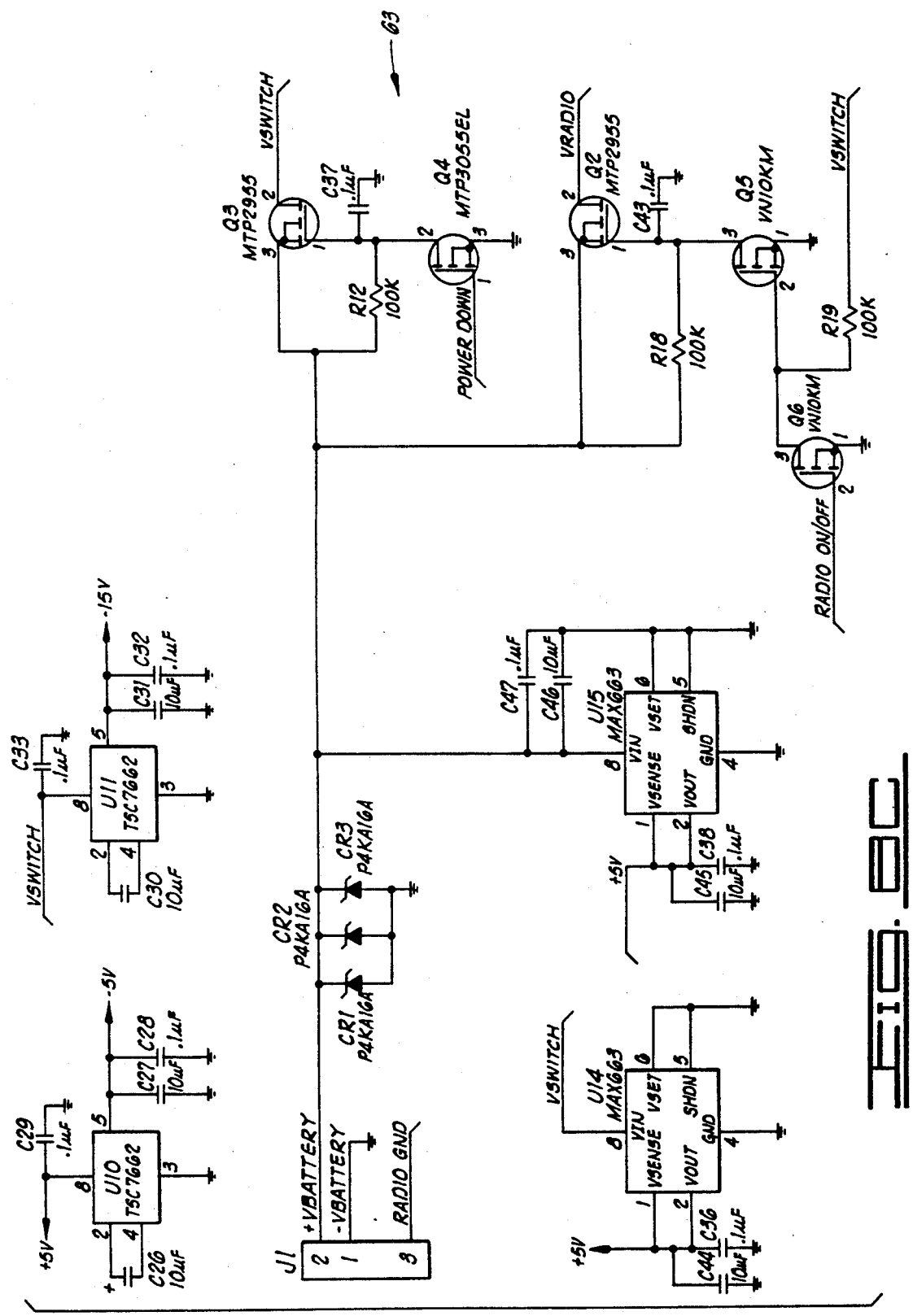

```
DISPLAY SELECT MENU

A - TANK STATUS    1, 2, 3, 4, 5, 6, 7, 8
B - TANK STATUS    9,10,11,12,13,14,15,16
C - TANK STATUS    17,18,19,20,21,22,23,24
D - TANK STATUS    25,26,27,28,29,30,31,32
E - TANK STATUS    33,34,35,36,37,38,39,40
F - TANK STATUS    41,42,43,44,45,46,47,48
G - TANK STATUS    49,50
H - COMM ERROR CODES
I - DEFINED TANK TYPES
J - PRESSURE SENSOR CALIBRATION
K - USER TANK PROFILE - 1
L - USER TANK PROFILE - 2
M - USER TANK PROFILE - 3
N - USER TANK PROFILE - 4

TRANSMITTER ON        RPS
```

FIG. 9

```
DISPLAY SELECT MENU

A - TANK LEVEL
B - TANK STATUS    1, 2, 3, 4
C - TANK STATUS    5, 6, 7, 8, 9, 10, 11, 12
D - TANK STATUS    13, 14, 15, 16, 17, 18, 19, 20
E - TANK STATUS    21, 22, 23, 24, 25, 26, 27, 28
F - TANK STATUS    29, 30, 31, 32, 33, 34, 35, 36
G - TANK STATUS    37, 38, 39, 40, 41, 42, 43, 44
H - TANK STATUS    45, 46, 47, 48, 49, 50
I - COMM ERROR CODES
J - DEFINED TANK TYPES
K - PRESSURE SENSOR CALIBRATION
L - USER TANK PROFILE - 1
M - USER TANK PROFILE - 2
N - USER TANK PROFILE - 3
O - USER TANK PROFILE - 4

TRANSMITTER ON    RPS
```

FIG. 10

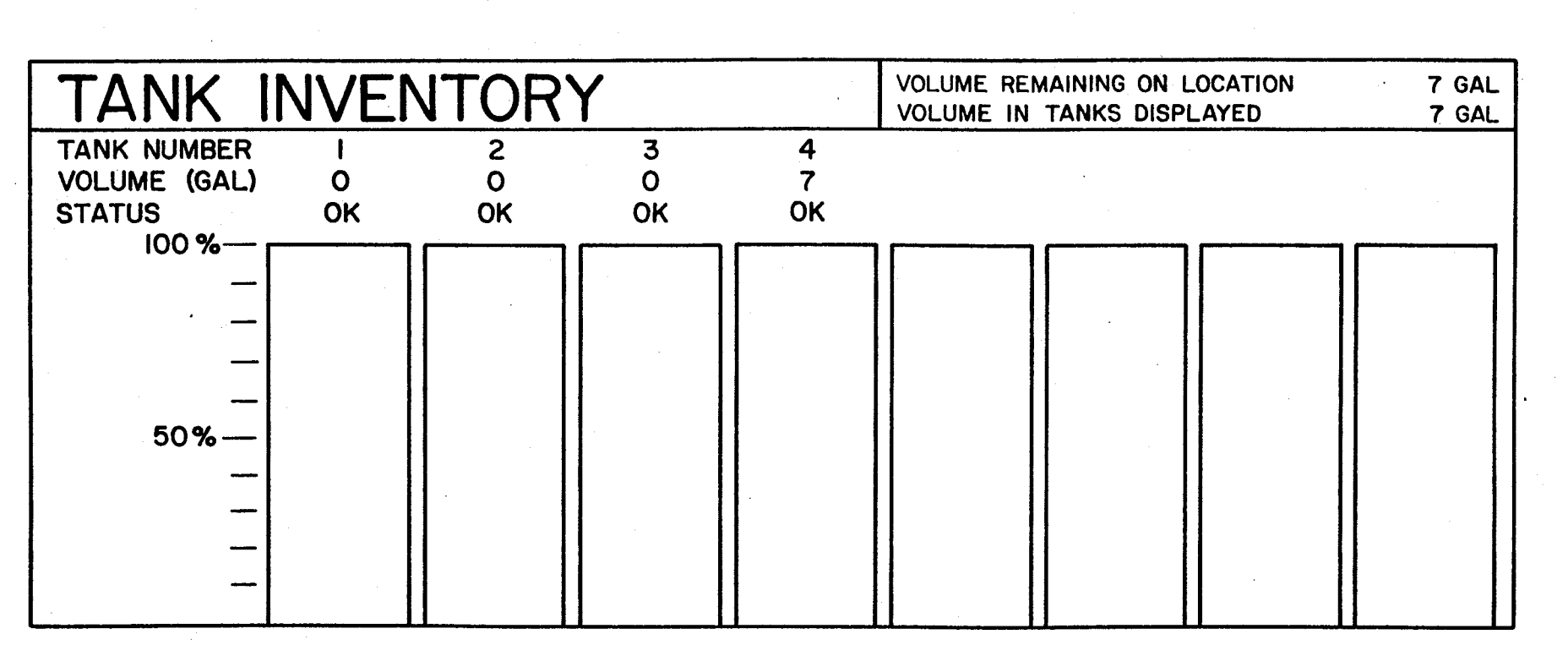

TANK INVENTORY

| TANK NUMBER | 1 | 2 | 3 | 4 | VOLUME REMAINING ON LOCATION | 7 GAL |
|---|---|---|---|---|---|---|
| VOLUME (GAL) | 0 | 0 | 0 | 7 | VOLUME IN TANKS DISPLAYED | 7 GAL |
| STATUS | OK | OK | OK | OK | | |

FIG. 11

| | 1 | 2 | 3 | 4 | | | | |
|---|---|---|---|---|---|---|---|---|
| TANK NUMBER | | | | | | | | |
| TIMER (SEC) | 142 | 154 | 213 | 79 | | | | |
| VOLUME (GAL) | 0 | 0 | 0 | 0 | | | | |
| PRESS (PSI) | -.03 | 0.00 | 0.00 | .01 | | | | |
| TANK TYPE | ADAMS | ADM FM500 | HALCO RB | HAL T75 | | | | |
| FLUID TYPE | UNDEFINED | UNDEFINED | UNDEFINED | UNDEFINED | | | | |
| ADD CONC | | | | | | | | |
| COMM STATUS | OK | OK | OK | OK | | | | |
| POLL TIMER | -128 | -117 | -58 | -191 | | | | |
| LEVEL (IN) | -1.1 | 0.0 | 0.0 | .2 | | | | |
| BATT STATUS | 12.9 | 12.4 | 13.2 | 13.2 | | | | |
| MSGS SENT | 124 | 61 | 140 | 124 | | | | |
| MSGS RCVD | 106 | 61 | 123 | 96 | | | | |
| SPEC GRAV | 0.000 | 1.000 | 1.000 | 0.000 | | | | |

TANK STATUS

FIG. 12

PRESSURE CALIBRATION

TANK NUMBER

ZERO        FEET

SPAN        FEET

SET RF TANK NUMBER

TURN OFF ALL UNITS

LOCAL RF TRANSMITTER IS ON      TRANSMITTER ON    RPS

FIG. 13

USER TANK PROFILE - 1

| H (IN) | V (GAL) | H (IN) | V (GAL) |
|--------|---------|--------|---------|
| 0      | 0       | 0      | 0       |
| 140    | 21000   | 0      | 0       |
| 0      | 0       | 0      | 0       |
| 0      | 0       | 0      | 0       |
| 0      | 0       | 0      | 0       |
| 0      | 0       | 0      | 0       |
| 0      | 0       | 0      | 0       |
| 0      | 0       | 0      | 0       |
| 0      | 0       | 0      | 0       |
| 0      | 0       | 0      | 0       |
| 0      | 0       | 0      | 0       |
| 0      | 0       | 0      | 0       |
| 0      | 0       | 0      | 0       |

EDIT HEIGHT (H) AND VOLUME (V) DATA WHERE H IS HEIGHT FROM THE BOTTOM OF THE TANK. THE DATA WILL BE SORTED BY HEIGHT AFTER EACH PAIR OF DATA POINTS IS MODIFIED AND ENTERED.

TRANSMITTER   ON   RPS

FIG. 14

APPARATUS, METHOD AND SYSTEM FOR MONITORING FLUID

MICROFICHE APPENDIX

A microfiche appendix (3 sheets containing 209 frames) is incorporated herein.

BACKGROUND OF THE INVENTION

This invention relates generally to apparatus, methods and systems for monitoring fluid in containers. The present invention relates more particularly, but not by way of limitation, to a radio-linked fluid monitoring system incorporating apparatus and method that use a single pressure sensor in a respective container to determine fluid level from which fluid volume can be automatically determined for different shapes of container.

To maintain an adequate fluid supply for a process which draws fluid held in a storage container, the amount of fluid in the container typically must be monitored. In the oil and gas industry, for example, a well sometimes needs to be fractured to enhance its productivity. Fracturing fluid to accomplish this is typically stored in one or more storage containers at the well site. The fluid is pumped out of the containers and into the well as needed. The operator in charge of the pumping needs to be aware of the various conditions of the pumping and fracturing process, one of which conditions is the amount of fluid remaining in the one or more containers.

One way to remain apprised of the amount of fluid is for the operator to visually or otherwise locally inspect each fluid container. This is not a desirable technique because of the potential safety hazard of being on or around the containers to inspect them and because of the time it would take to inspect the containers.

To alleviate the foregoing shortcoming, there are automated devices for measuring fluid levels in containers. These can use various techniques, but the one relevant to our invention described below uses fluid pressure for determining the amount of fluid in the container. The pressure responsive techniques we are aware of use two pressure sensors to determine fluid level. One type uses one differential pressure transducer to determine density and one gauge pressure transducer to sense pressure at the bottom of the body of fluid. Another type uses two gauge pressure transducers; outputs from the two pressure transducers spaced a known distance apart are used to compute density, and the output from one of the pressure transducers provides the total fluid pressure which is divided by the determined density to give a quotient specifying the level of the fluid in the container. The transducers of these systems we are aware of are fixed to the containers (e.g., attached to the side wall of the container below the surface of the contained fluid) so that they cannot be readily moved (e.g., container must be drained before transducers can be detached). Such systems can provide for remote communications of data via wire or radio frequency transmission.

Although the foregoing automated devices and systems can provide advantages over types requiring local inspections by an operator, there is still the need for an improved automated apparatus. There is the need for a fluid monitoring apparatus which uses only a single pressure sensor, thereby obviating the cost of the second sensor used in the aforementioned devices. There is the need for a fluid monitoring apparatus which is easy to use with different types of containers. For example, the apparatus preferably should be portable and adaptable for use with different shapes of containers. That is, the apparatus should be able not only to calculate the height of the fluid in a container, but also to convert that height into the correct volume, which can be different from one shape of container to another for the same calculated height. There is also the need for a fluid monitoring method and system which meet these same needs and which permit remote communication and control.

SUMMARY OF THE INVENTION

The present invention overcomes the above-noted and other shortcomings of the prior art by providing a novel and improved fluid monitoring apparatus, method and system which meet the aforementioned needs.

The present invention provides an apparatus for monitoring fluid in a container, comprising: one, and only one, pressure sensor adapted to be moved in the container and the fluid therein; and means for receiving signals from the pressure sensor in response to, and as readings of, pressure sensed by the pressure sensor and for determining density of the fluid in response to two readings from the pressure sensor and for determining the level of the fluid in the container in response to the determined density of the fluid and a third reading from the pressure sensor. In a preferred embodiment, the present invention provides an apparatus for monitoring fluid in a selected one of a plurality of different containers, comprising: a reel adapted to be rotated relative to a selected container; an electrical cable mounted on the reel; one, and only one, pressure sensing means for sensing pressure in the fluid, the pressure sensing means connected to the electrical cable; a battery disposed in the reel; and electrical circuit means, connected to the battery and disposed in the reel, for automatically determining, regardless of the shape of the selected container, the level and volume of the fluid in the selected container in response to pressures sensed by the pressure sensing means throughout the fluid in the selected container as the pressure sensing means is moved within the fluid on the cable.

The present invention also provides a method of monitoring fluid in a container, comprising: (a) sensing with a pressure sensor the pressure of the fluid at a first depth of the fluid; (b) sensing with the pressure sensor the pressure of the fluid at a second depth of the fluid, which second depth is a known distance from the first depth; (c) sensing with the pressure sensor the pressure of the fluid at the bottom of the fluid; (d) determining the density of the fluid in response to the pressures sensed in steps (a) and (b); and (e) determining the height of the surface of the fluid in the container in response to the pressure sensed in step (c) and the density determined in step (d). This method preferably further comprises determining the volume of fluid in the container in response to the determined height, including retaining in a memory, located with the pressure sensor, conversion tables correlating volume with height for a plurality of containers, and retrieving from the memory the volume correlated with the height determined in step (e) for the respective container.

The present invention further provides a fluid monitoring system, comprising: a plurality of fluid containers disposed at a well site; a plurality of fluid measuring devices, each of the devices mounted adjacent a respective container and each of the devices including: one, and only one, pressure sensor adapted to be moved in the respective container and the fluid therein and to provide signals in response to pressure; computer means for receiving signals from the pressure sensor in response to, and as readings of, pressure sensed by the pressure sensor and for determining density of the fluid in the respective container in response to two readings from the pressure sensor and for determining the amount of the fluid in the respective container in response to the determined density of the fluid and a third reading from the pressure sensor; and a first radio connected to the computer means; and an operator interface device located remotely from the fluid containers and the fluid measuring devices, the operator interface device including a second radio for communicating with each first radio to receive therefrom encoded signals representative of the amount of fluid in the containers.

An advantage of the present invention is that it uses one, and only one, pressure sensor with regard to monitoring the amount of fluid in any one container. Furthermore, the present invention is portable and is adapted to monitor fluid in different shapes of containers. This adaptability is available in the apparatus which is located at the container. Thus, multiple container configurations can be accommodated with a single such apparatus. The apparatus operates without requiring on-going direct local control by an operator after the apparatus has been set-up and initialized. This is desirable from a safety standpoint because no one is required to be on or around the container or containers monitored by the present invention (however, the preferred embodiment does permit such direct local control). Remote communications between a local monitoring apparatus and a remote operator interface device are preferably via radio links so that no cables need to be run across long distances which might separate the apparatus and operator interface device. This is particularly advantageous when several apparatus are used in combination with an operator interface device.

Therefore, from the foregoing, it is a general object of the present invention to provide a novel and improved apparatus, method and system for monitoring fluid in one or more containers. Other and further objects, features and advantages of the present invention will be readily apparent to those skilled in the art when the following description of the preferred embodiment is read in conjunction with the accompanying drawings.

BRIEF DESCRIPTION OF THE DRAWINGS

FIG. 7 is a schematic circuit and block diagram of the electrical features of the apparatus shown in FIG. 4.

FIGS. 8A-8C are a schematic circuit diagram of the circuit for the printed circuit board shown in FIG. 7.

FIGS. 9-14 illustrate various displays output by the operator interface device during operation of the preferred embodiment apparatus, method and system of the present invention.

DETAILED DESCRIPTION OF PREFERRED EMBODIMENT

Figure 1:
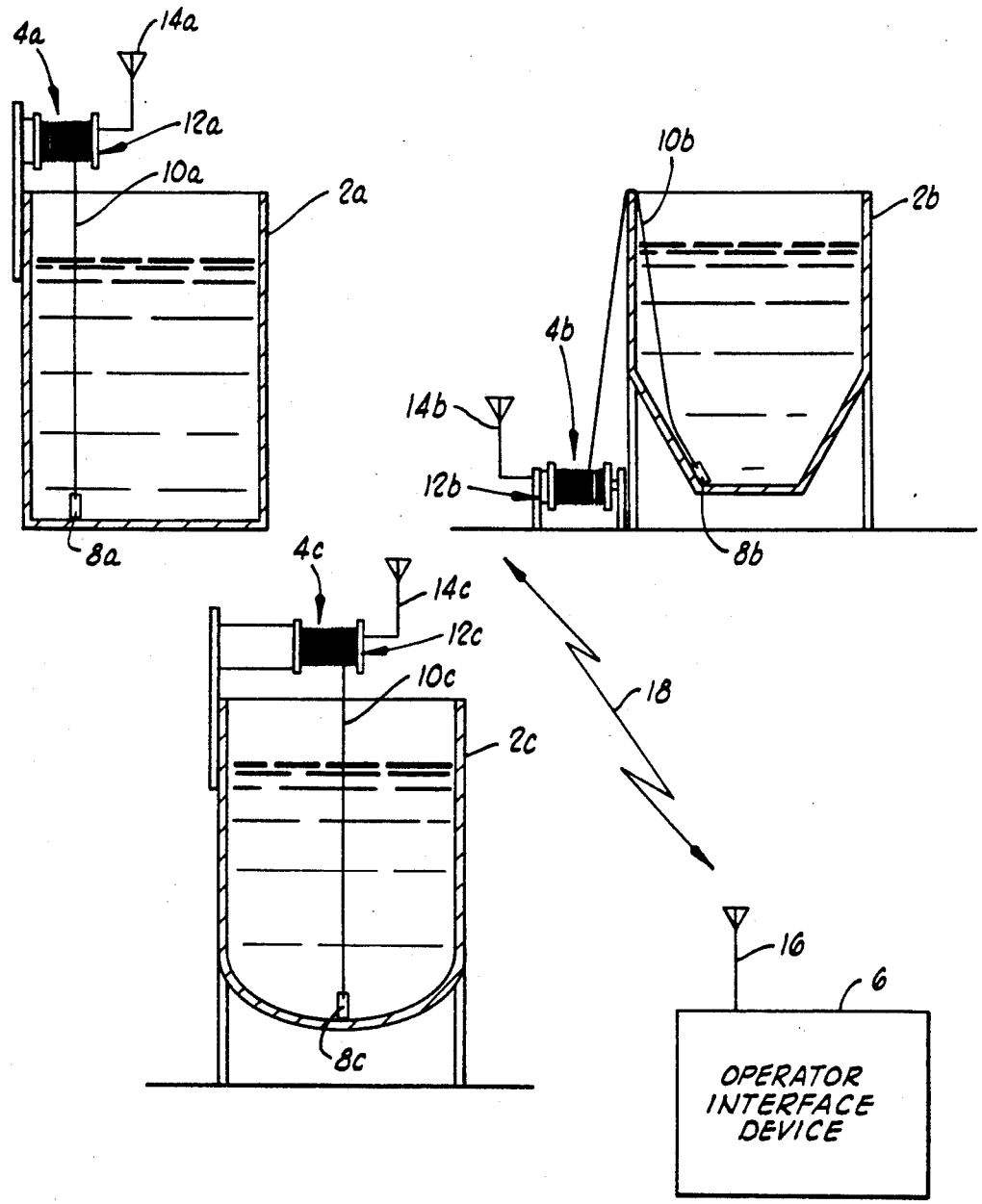
FIG. 1 is a schematic and block diagram illustrating several apparatus of the present invention associated with containers and in radio communication with an operator interface device.

Referring to FIG. 1, the fluid monitoring system of the present invention includes a plurality of fluid containers 2, a plurality of fluid measuring devices 4, and an operator interface device 6 (different units of the same type of device are designated by the same reference numeral but different letter). It is to be noted, however, that the present invention also pertains more generally to any one of the fluid measuring devices as a stand-alone apparatus. The overall system as illustrated in FIG. 1 will be described first, followed by descriptions of the operator interface device 6, the fluid measuring device 4 and the methodology and operation of the present invention.

The fluid containers 2 can have different shapes and capacities. Flat-, angular- and curved-bottom containers are illustrated in FIG. 1 by way of example.

Shown in FIG. 1 to be associated with each container 2 is a respective fluid measuring device 4; however, one device 4 of the present invention can be used with more than one container. That is, each fluid monitoring device 4 of the preferred embodiment is portable so that it can be carried from one container to another, and each such device is able to compute both the level (i.e., total height or depth) and the volume of fluid in different shapes of containers. The device 4 can be associated with a respective container 2 in any suitable manner which allows a probe 8 and connected electrical cable 10 to be unreeled from a reel 12 and lowered to the bottom of the container. For example, the device 4 can be connected to the container, it can be disposed above the container, and it can be put on the ground beside the container.

Although each device 4 can function as a stand-alone unit, it can also function with the operator interface device 6 so that, once the devices 4 have been set up and initialized and the probes lowered to bottom, an operator does not need to be physically located at the containers 2 or devices 4 to be advised of the amounts of fluid in the containers 2. In the preferred embodiment, each device 4 communicates with the operator interface device 6 via a radio link illustrated in FIG. 1 by the fluid monitoring device antennas 14 and the operator interface device antenna 16. Communications are bidirectional, as indicated by double-arrow line 18, in the preferred embodiment wherein the operator interface device 6 polls each fluid monitoring device 4 to control when each device 4 transmits signals encoded with information about the monitored amount of fluid. The operator interface device 6 thus functions as both a display terminal for displaying information from the devices 4 as well as a controller for controlling any of the devices 4 being used; however, as previously stated, the operator interface device 6 is not necessary to the local monitoring function performed by each fluid monitoring device 4 individually.

Figure 2:
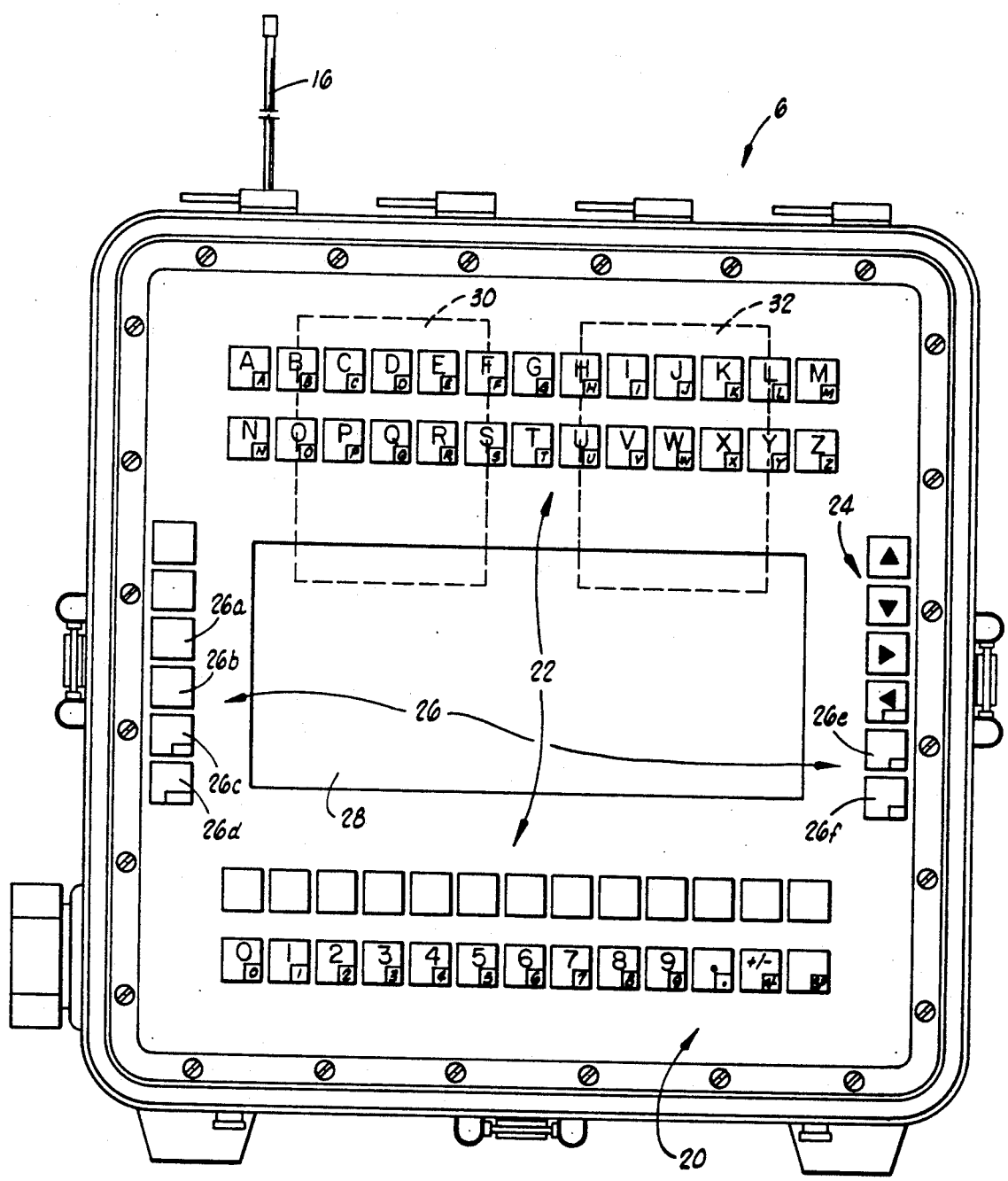
FIG. 2 is a front exterior view of the preferred embodiment of the operator interface device.
Figure 3:
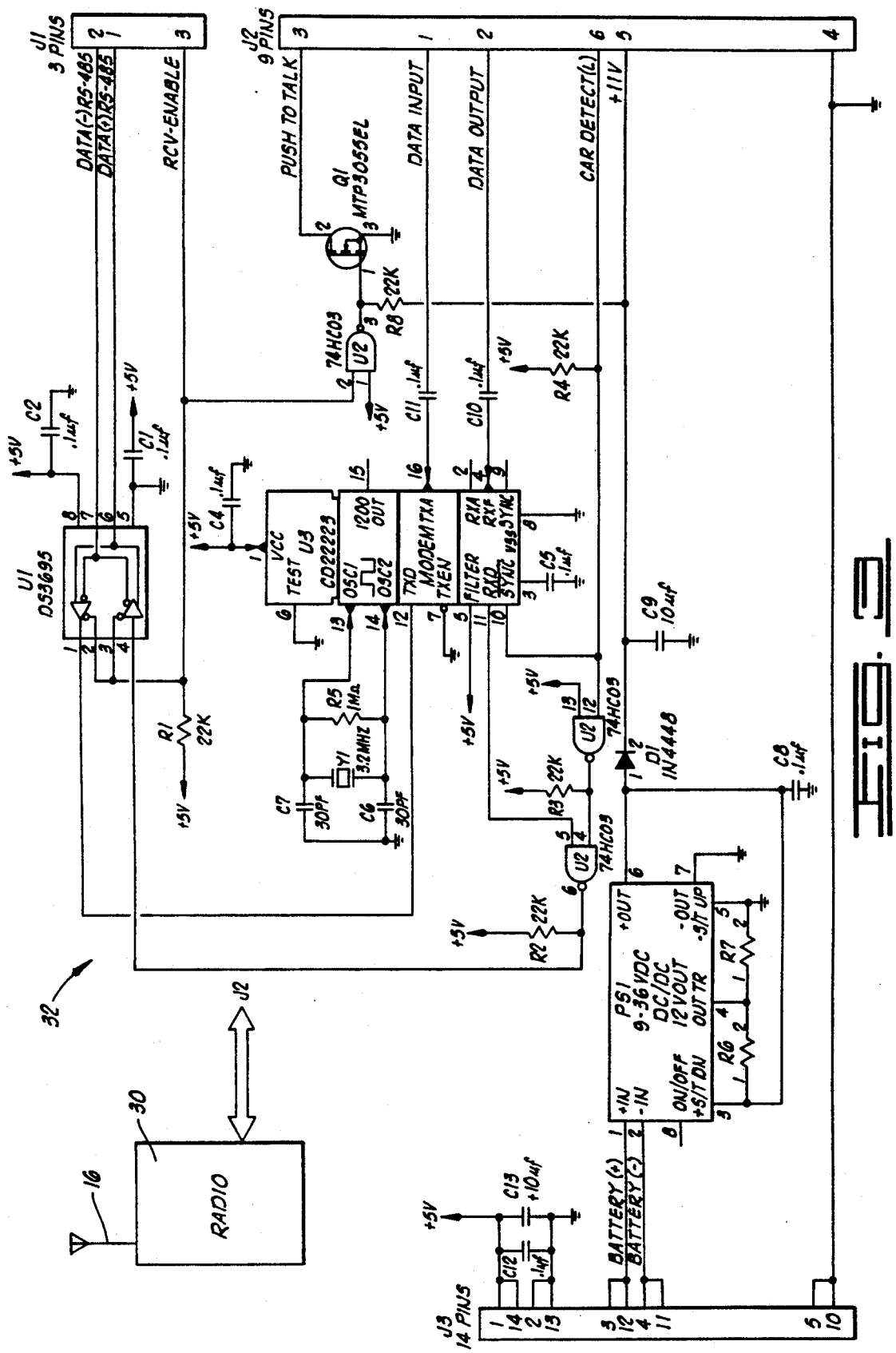
FIG. 3 is a schematic circuit diagram of a modem circuit used in the operator interface device for communicating with a fluid monitoring apparatus of the present invention.

Referring to FIGS. 2 and 3, the preferred embodiment of the operator interface device 6 will be described. The device 6 includes a keyboard and display panel 20 through which an operator inputs and receives information. The panel 20 and the overall interface device 6 are substantially the same (differences will be described hereinbelow with reference to FIG. 3) as the Operator Interface Panel of the Halliburton Services ARC System. The panel 20 includes alphanumeric keys 22, directional arrow keys 24, function keys 26 (scroll list key 26a, units key 26b, display key 26c, cursor key 26d, reset key 26e, enter key 26f) and display 28. In the preferred embodiment, the operator interface device 6 can communicate with up to fifty fluid monitoring devices 4.

Communication in the preferred embodiment is by the aforementioned radio link involving radio frequency signals transmitted between the operator interface device 6 and the active fluid monitoring devices 4 which are within range (e.g., 1-2 miles). It is this radio communication capability that distinguishes the device 6 from the typical Operator Interface Panel (OIP) of the Halliburton Services ARC System. This capability is implemented by adding the circuit and radio illustrated in FIG. 3 to the conventional OIP. In the preferred embodiment, the operator interface device 6 includes a Maxon DM-0530 data radio 30 (UHF, two watts, 467.8 MHz crystal) having the antenna 16. The device 6 also additionally includes a 1200 baud frequency-shift keying (FSK) modem circuit 32 connected to the radio 30 for properly formatting data to be transmitted by the radio 30 or received thereby.

Figure 4:
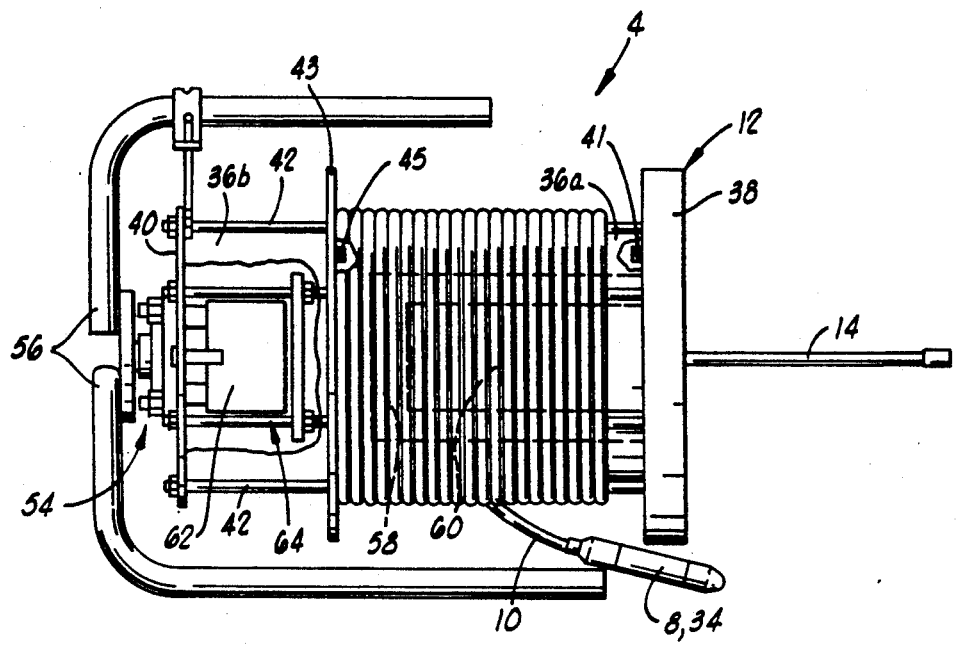
FIG. 4 is a side view of the preferred embodiment of the fluid monitoring apparatus of the present invention.
Figure 5:
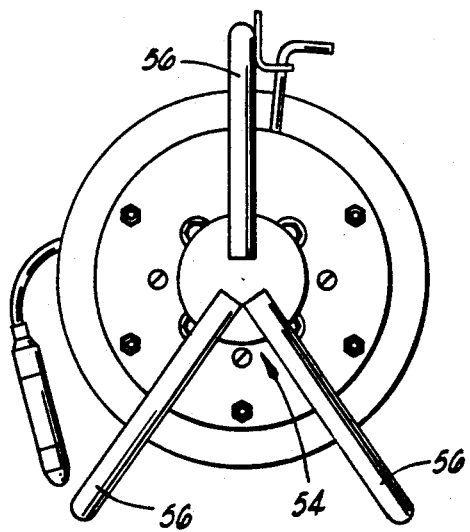
FIG. 5 is an end view of the apparatus shown in FIG. 4.
Figure 6:
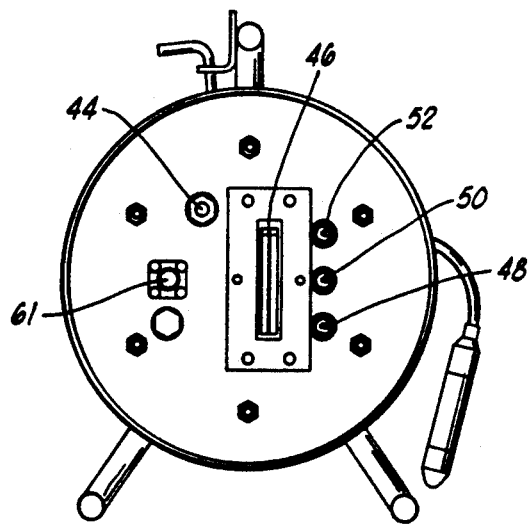
FIG. 6 is another end view of the apparatus shown in FIG. 4.

Referring next to FIGS. 4-8, the preferred embodiment apparatus for implementing the fluid monitoring device 4 will be described. Referring initially to FIGS. 4-6, each device 4 includes one, and only one, pressure sensor 34 adapted to be moved in the container and the fluid therein. The pressure sensor 34 is a pressure transducer contained in the probe 8 connected at the end of the electrical cable 10 illustrated in FIG. 1. In a particular embodiment, the pressure sensing means includes a 0-10 psig submersible pressure transducer model PDCR950TI from Druck, Inc.

The pressure sensor 34 is supported by the cable 10 and the reel 12 upon which the cable 10 is wound. The cable is of suitable length to accommodate the size of the containers 2 with which it is contemplated to be used and to accommodate the electrical connections needed between the pressure sensor 34 and the electrical circuit means contained inside the reel 12 as subsequently described.

The reel 12 is adapted to be rotated relative to a selected container 2 with which it is to be used. This allows the cable 10 to be unreeled and the pressure sensor 34 to be lowered into the selected container 2. The reel 12 has a hollow cylindrical body 36 which includes separate front and rear compartments or housings 36a, 36b connected between two end members 38, 40 by a plurality of external tie rods 42. The cable 10 is wound around the body 36 and tie rods 42.

The front housing 36a is fluid tightly sealed against front end member or panel 38 by an O-ring seal 41, and it is fluid tightly sealed against a middle panel 43 by an O-ring seal 45. Fluid entry through the cable 10 is prevented or limited by a desiccant cartridge (not shown) connected within the cable 10.

The circular end member 38 supports a connector 44 for the antenna 14, and it supports a display 46 and switches 48, 50, 52 for providing local display and control means. The circular end member 40 is connected to a bearing 54 attached to a frame 56 so that the reel can rotate relative to the frame 56 and an object to which the frame 56 is fixed (e.g., a container, the ground).

Contained in the hollow interiors of the main reel body 36 are a circuit board 58, a radio 60 and a battery 62 as shown in FIGS. 4 and 7. The battery 62 energizes the electrical components and circuits within the reel 12. The battery 62 is housed in the compartment 36b; it is supported by a bracket assembly 64 (FIG. 4). The printed circuit board 58 and the radio 60 are housed in the compartment 36a. With regard to the preferred embodiment circuits of the board 58 as shown in FIG. 8, the battery 62 is connected to the power regulating and switching circuit 63 (FIG. 8C). The battery 62 is preferably rechargeable, which is provided for in the FIG. 7 embodiment through recharger connector 61 mounted on the front end panel 38.

Contained on the circuit board 58 are electrical circuit means for automatically determining, regardless of the shape of the selected container 2, the level and volume of the fluid in the selected container in response to pressures sensed by the pressure sensing means 34 throughout the fluid in the selected container as the pressure sensing means is moved within the fluid on the cable 10. This includes means for receiving signals from the pressure sensor in response to, and as readings of, pressure sensed by the pressure sensor and for determining density of the fluid in response to two readings from the pressure sensor and for determining the level of the fluid in the container in response to the determined density of the fluid and a third reading from the pressure sensor.

Figure 8A:
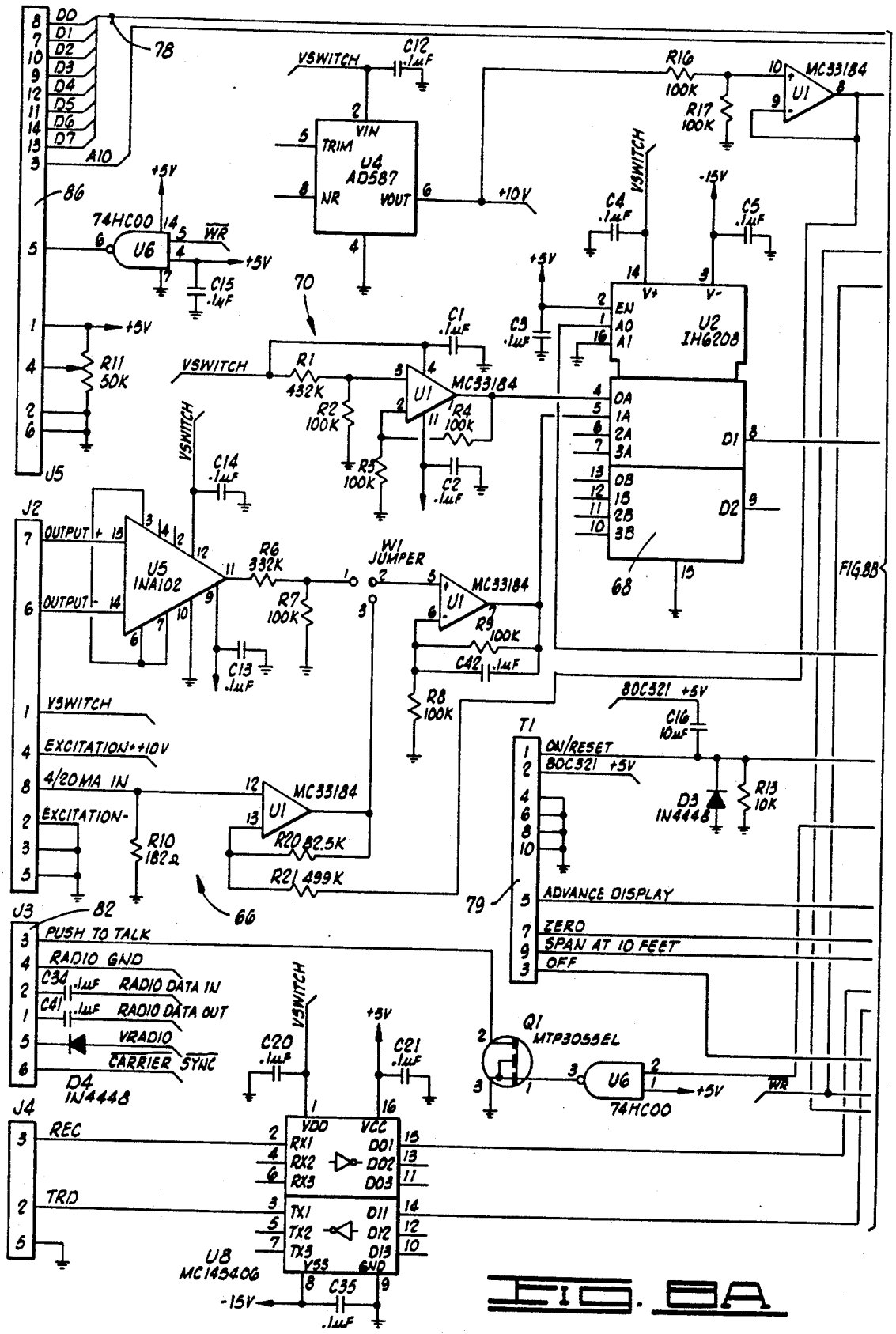

Referring to FIG. 8A, the signal from the pressure sensor 34 is received through the cable 10 by a signal conditioning circuit 66. The conditioned signal output from the circuit 66 is provided to a dual channel multiplexer 68. Another input of the multiplexer 68 is connected to a circuit 70 monitoring the voltage "VSWITCH."

Figure 8B:
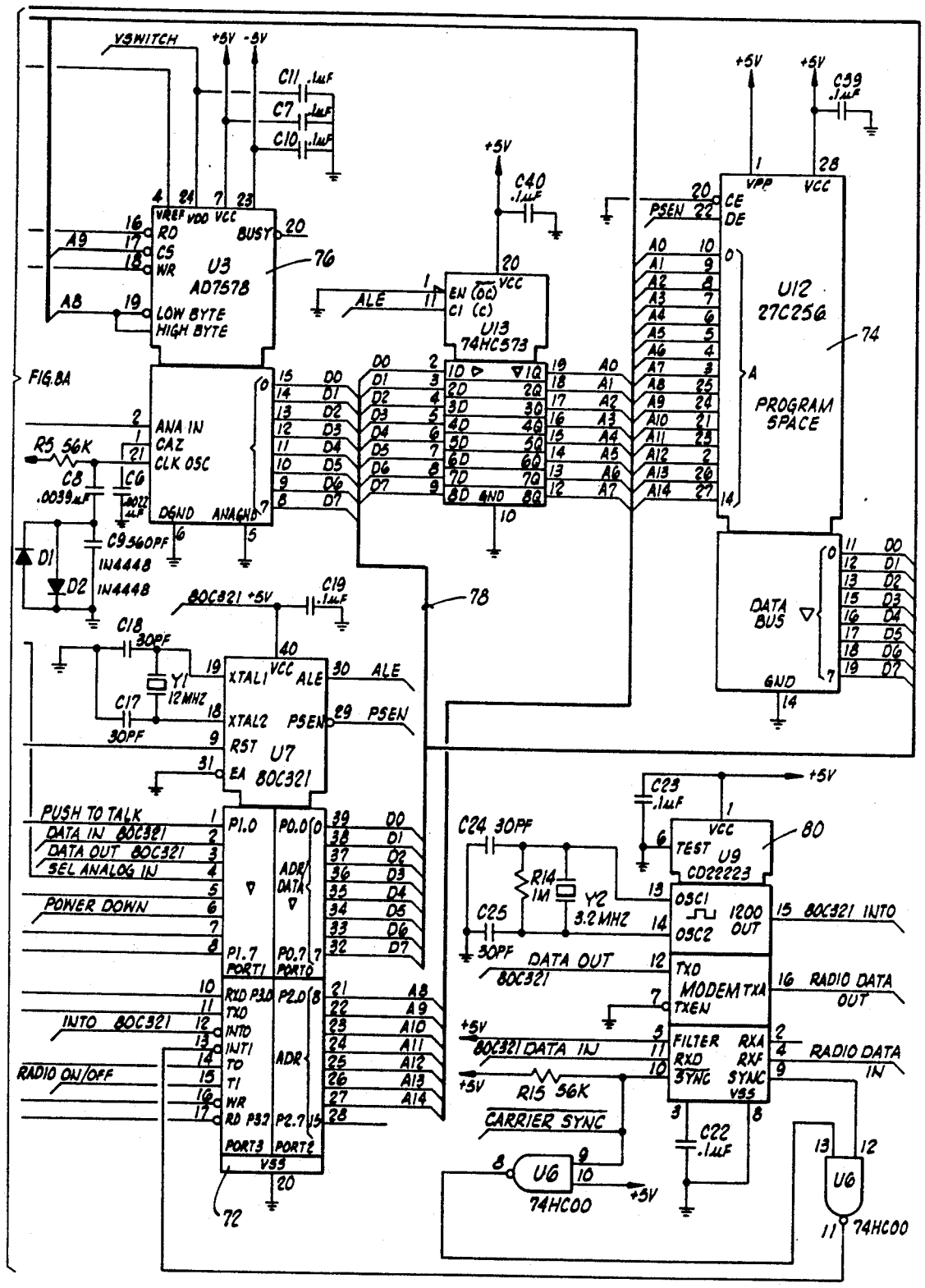

Referring to FIG. 8B, a microprocessor-based microcontroller 72, responsive to a program stored in a preprogrammed memory 74, selects the channel of the multiplexer 68 to be output to an analog-to-digital converter 76. The digital output from the analog-to-digital converter 76 is communicated to the microcontroller 72 via a data bus 78. When the signal received by the microcontroller 72 is one representing sensed pressure, it is stored in a random access memory internal to the microcontroller 72. The stored signals are used to determine density and fluid level as subsequently described. The term "memory" as used herein encompasses both the aforementioned memories of the preferred embodiment.

The electrical circuit means also includes means for converting the determined fluid level into a signal representing the fluid volume. This means includes the memory 74 because it contains signals encoded to define volumes correlated to heights of fluid for the plurality of different shapes of containers with which the device 4 is preset. In a particular implementation, the memory 74 is programmed with a table correlating fluid volumes (e.g., gallons) to fluid heights (e.g., inches) for fifteen different shapes of containers; however, additional shapes can be accommodated by additional preset memory or by manual entries using the microcontroller 72.

In view of the microcontroller 72 and the programmed memory 74, the foregoing are implemented at least in part by computer means for receiving signals from the pressure sensor in response to, and as readings of, pressure sensed by the pressure sensor and for determining density of the fluid in the respective container in response to two readings from the pressure sensor and for determining the amount of the fluid in the respective container in response to the determined density of the fluid and a third reading from the pressure sensor. Specifically, fluid height is calculated by the microcontroller 72 from the pressure readings, and fluid volume is determined from the conversion tables in the memory 74. Local external operation of the microcontroller 72 is effected via the switches 48, 50, 52 (FIGS. 6 and 7) connected to the microcontroller 72 via a connector 79 (FIG. 8A).

The locally computed data indicating the amount of the monitored fluid can be communicated to a remote location by the radio 60 (FIG. 7) which provides means for transmitting an encoded signal representing the determined fluid level (and/or fluid volume). The radio 60 is disposed in the reel 12 and connected to the electrical circuit means so that encoded signals representing at least the determined level of fluid can be transmitted by the radio 60 to a location remote from the apparatus. For the preferred embodiment circuit shown in FIG. 8, the radio 60 is connected to and controlled by the microcontroller 72 and modem 80 (FIG. 8B). Connections with the radio 60 are made through a connector 82 and intervening circuitry as shown in FIG. 8A.

Computed data can be displayed locally through the display 46 which provides means for selectably displaying the microcontroller-determined fluid level and the memory-stored correlated volume. The display 46 is connected by conductors 84 (FIG. 7) and connector 86 (FIG. 8A) to the data bus 78 and power components as shown in FIG. 8A. The display 46 is mounted on the end panel 38 of the reel 12 as described above.

Use of the fluid monitoring apparatus just described, and the method of the present invention, includes sensing with the pressure sensor the pressure of the fluid at a first depth of the fluid. In the preferred embodiment, this includes moving the single pressure transducer 34 to the upper surface of the fluid in the selected container 2 by suspending the single pressure transducer 34 on the electrical cable 10 from the reel 12, and recording the pressure sensed at the surface. The sensed pressure is stored as an encoded signal in the memory of the microcontroller 72 contained inside the reel 12.

The method further comprises sensing with the pressure sensor the pressure of the fluid at another depth of the fluid which is a known distance from the first depth. In the preferred embodiment, this includes lowering the single pressure transducer 34 a predetermined distance (e.g., three feet) into the fluid in the container 2 by unreeling an additional length of the cable 10 from the reel 12. This second sensed pressure is recorded by storing a second encoded signal in the memory of the microcontroller 72 contained inside the reel 12.

The method of the present invention further comprises sensing with the pressure sensor the pressure of the fluid at the bottom of the fluid. In the preferred embodiment, this includes lowering the single pressure transducer 34 to the bottom of the fluid by unreeling more of the cable 10 from the reel 12 until the single pressure transducer 34 is on the bottom of the container. The pressure sensed at the bottom is recorded by storing a third encoded signal in the memory of the microcontroller 72 contained inside the reel 12.

The method further comprises determining the density of the fluid in response to the pressures sensed at the first depth (e.g., at the surface) and at the second distance, (e.g., a predetermined distance below the surface). In the preferred embodiment, this includes using the microcontroller 72 inside the reel 12 for computing from the first and second encoded signals the quotient obtained by dividing (1) the difference between the recorded pressures sensed at the surface and at the predetermined second depth by (2) the predetermined intervening distance.

The method further comprises determining the height of the surface of the fluid in the container in response to the pressure sensed at the bottom of the container and the density determined as just described. In the preferred embodiment, the height is determined using the microcontroller 72 inside the reel 12 for computing the quotient of the recorded pressure defined by the third stored encoded signal divided by the previously calculated density.

The method further comprises determining the volume of fluid in the container in response to the determined height. This includes retaining in the memory 74 conversion tables correlating volume with height for a plurality of shapes of containers, and retrieving from the memory 74 the volume correlated with the height determined as just described. In the preferred embodiment, the microcontroller 72 inside the reel 12 is programmed for retrieving from the stored table contained in the memory 74 for the particular container 2 a respective encoded signal representing the volume correlated to the computed height and the particular container.

In the preferred embodiment, the method further comprises transmitting an encoded radio frequency signal representing the determined height to a location remote from the monitored container. In the preferred embodiment, the transmission is made from the radio 60 as directly controlled by the microcontroller 72 and modem 80, but such direct control is not initiated in the preferred embodiment until a radio frequency control signal is received by the microcontroller 72, through the radio 60, from the location remote from the container and fluid monitoring apparatus (i.e., from the operator interface device 6 in the preferred embodiment).

The foregoing general methodology and the following more specific methodology can be implemented by programming the microcontroller 72 with a program written using known programming skills to implement the procedure described herein and stored in known manner in the memory 74. An example of such a program is listed in the microfiche appendix incorporated herein.

A more detailed explanation of the operation of a particular implementation of the operator interface device 6 and the fluid monitoring devices 4 follows. Although the utility of the present invention in its broader aspects is not limited to the oil and gas industry, the following more detailed description will be made with reference to the containers 2 being tanks holding fracturing fluid at a well site. Such tanks and use are well-known in the industry. Although the present invention is not so limited, typically there would be up to ten or so such tanks at a well site. Again without limiting the present invention, examples of such tanks include: Adams Frac Master 500 BBL; Adams Frac Miser 500 BBL; Halco Round Bottom 500 BBL; Halco DBL Comp Round Bottom Front; Halco DBL Comp Round predetermined distance between the aforementioned first and second depths) via the operator interface device 6. If the tank was calibrated locally at the respective fluid monitoring device 4, this field will not be updated. This field gives the calculated specific gravity of the fluid given the zero and span.

6) TIMER—the timer will count up to 90 seconds. The operator interface device 6 will then transmit a radio frequency message to the fluid monitoring device 4 of the corresponding tank and if there is no answer, the timer will be reset to zero and it will count up to 90 again. If a fluid monitoring device 4 answers, then the screen will automatically switch to the Tank Level page and the corresponding tank will be placed on the active tanks list. For tanks on the active tanks list, the timer will count up and will not reset to zero until the next message is received from the respective fluid monitoring device 4 (as a result of the aforementioned expired poll timer and the resulting polling by the operator interface device 6).

7) COMM STATUS—this will indicate to the operator the condition of the communication between the operator interface device 6 and the fluid monitoring device 4 of the corresponding tank.

8) MSGS SENT—this will keep track of the number of transmissions that the operator interface unit 6 has tried. Each time the TIMER is reset to zero, this counter will increment indicating that a radio frequency message was transmitted.

To control remote calibration, a screen as illustrated in FIG. 3 is provided for entering the following data:

1) TANK NUMBER—this field determines which of the tanks (numbered 1-50) will be zeroed or spanned. To enter a number, press the cursor key 26d and the appropriate up and down arrow keys 24 to move to this field. While holding the cursor key 26d down, press the appropriate numeric keys and press the enter key 26f. The tank number is necessary only to zero or span. Once the tank number is entered, the message "ready to accept commands" will be displayed on the screen.

2) ZERO—after entering the tank number of the tank to be zeroed, the tank can be zeroed at 0 (or any feet) by holding the cursor key 26d and entering the desired zero value and pressing the enter key 26f. Once the zero command is entered the message "zero command waiting to be sent." will be displayed and the operator interface device 6 will transmit the command at the expiration of the poll timer. When the respective fluid monitoring device 4 receives the command, it will echo the command back to the operator interface device 6 and the operator interface device 6 will display the new zero to the right of the zero field. This feedback will indicate that the fluid monitoring device 4 has received the command correctly.

3) SPAN—a tank can be spanned at some value (in feet) by holding the cursor key 26d and entering the desired span value and pressing the enter key 26f. Once the span command is entered, the message "span command waiting to be sent." will be displayed and the operator interface device 6 will transmit the command at the expiration of the poll timer. When the fluid monitoring device 4 receives the command, it will echo the command back to the operator interface device 6 and the operator interface device 6 will display the new span to the right of the span field. This feedback will indicate that the device 4 has received the command correctly.

4) SET RF TANK NUMBER—the operator interface device 6 can be used to change the tank number of a particular tank. To do so, cursor down to this field and enter the new tank number making sure that the fluid monitoring device 4 to be changed is the only one on. This is important because the command to change the tank number is a global command and thus all fluid monitoring devices that are on will receive it. Hence if more than one tank is on, those tanks will have the same tank number.

5) TURN OFF ALL UNITS—the operator interface device 6 can be used to turn off all the fluid monitoring devices 4 remotely. To do so, simply cursor down to this field and press the enter key 26f. There are no numbers to type in—this is a global command and thus all listening fluid monitoring devices 4 will turn off.

6) LOCAL RF TRANSMITTER—this field allows the operator to turn the transmitter on the operator interface device 6 either off or on. Care must be exercised when turning the transmitter on (or off) due to the fact that radio frequency conflicts can occur if more than one operator interface device 6 is being used. This is due to the need that there only be one master in a master-slave system.

FIG. 14 shows the screen for entering a fluid height-to-fluid volume conversion table for a tank not previously included in the memory 74. In the present particular embodiment, the tables for the additional tank types are not supported in the memory 74 due to memory constraints. When the tank type on the operator interface device 6 is different from the tank type on the fluid monitoring device 4, the volume displayed on the operator interface device 6 does not correspond with the volume displayed on the fluid monitoring device 4. The level of fluid (in inches or meters) should be the same, however. Use the cursor key 26d, the arrow keys 24, and the numerical keys to enter the height (in inches or meters from the bottom of the tank) and the volume corresponding to that height. The data will be sorted by height after each pair of data points is modified and entered.

As stated before, the fluid monitoring devices 4 are considered slave devices in a master-slave system. As a result, each fluid monitoring device 4 does not transmit any information until it has received a request from the master operator interface device 6. On the top right-hand side of the 2-line LCD screen 46 of each fluid monitoring device 4, there is a status field that tells the operator the current condition of the fluid monitoring device 4. The messages displayed there can be any one of the following:

1) ID—this message, which stands for idle, indicates that the fluid monitoring device 4 has turned off its transmitter. There are two reasons for the fluid monitoring device 4 to display this message:

a) the operator interface device 6 has issued a sleep command and the fluid monitoring device 4 is in sleep mode. As noted earlier, sleep mode is issued when the level in the tank stays constant for a long period of time (about 14 minutes). This mode is mainly used for battery power conservation.

b) the fluid monitoring device 4 does not recognize or "hear" any communications from any device (operator interface device 6 or other fluid monitoring device 4). This condition arises when there is no operator interface device 6 or there is a communications problem between the operator interface device 6 and the fluid monitoring device 4 that prevents the fluid monitoring device 4 from "hearing" anything.

2) BLANK—If this field is blank, then the fluid monitoring device 4 is usually in a normal operating mode. It "hears" messages from other operator interface device 6-fluid monitoring device 4 communications and it has not received a command to go to sleep.

3) TX—this message, which stands for transmit, comes up when the fluid monitoring device 4 receives a message and it is transmitting a message back. The TX message will disappear as soon as the message has been sent.

The following is how to operate a respective fluid operating device 4:

measure fluid level a) Place the probe 8 into the fluid to be measured, allowing the probe to reach the temperature of the fluid.

b) Raise the probe 8 out of the fluid and press the key 50 on the end of the reel 12 to "zero" the unit. This calibrates the zero inches of fluid reading.

c) Lower the probe 8 until a float attached to the cable 10 is felt hitting the top of the fluid and press the key 50 to "span.". This is the second calibration point.

d) Drop the probe 8 to the bottom of the tank.

Calibration of specific gravity

Repeat the operations procedure above in a tank of water (specific gravity of 1). Press the "advance display" key 52 until the second line reads "set s.g. to water (1)". Pressing the "span" key 50 will set the specific gravity to one. Calibrating on any other fluid will calculate the specific gravity of that fluid as compared to this calibration of water.

Selecting the tank type

Several tank types are defined in the memory 74 of the device 4. The tank type can be selected by selecting the tank type on the operator interface device 6 or locally on the fluid monitoring device 4 by:

a) Advancing the display (pressing the "advance display" key 52) to read out the volume of fluid and a tank type; or b) Pressing the key 50 until the desired tank type is displayed.

Spanning the sensor somewhere other than at the float

The sensor can be zeroed or spanned at any depth from the operator interface device 6. Locally the sensor can be spanned at any depth from 1 to 9 feet by:

a) Advancing the display (pressing the "advance display" key 52) until the second line reads "press span at x feet".

b) Pressing the key 50 to "zero" will advance the depth from 1 to 9 feet.

c) Pressing "span" on key 50 with "press span at 9 feet" will span the sensor at 9 feet assuming the probe is 9 feet below the surface of the fluid.

Local bar graph indication

A local bar graph can be displayed by pressing "reset" on the key 58 or by pressing the "advance display" key 52 until the second line shows a horizontal bar graph or is blank. This bar graph is in inches with one character equal to 5 inches.

Changing units

The units can be changed from inches to meters and meters to inches by:

a) Advancing the display (pressing the "advance display" key 52) until the second line reads "chg units".

b) Pressing the key 50 to "SPAN."

Battery status

The status of the 12-volt rechargeable battery can be checked by:

a) Advancing the display until the second line reads "x-tank xx.x-V" where x is the tank number and xx.x is the voltage of the battery.

b) The voltage should be kept at 12 volts or higher for proper operation (using the battery charger).

Changing the tank number

The tank number may be changed by:

a) Advancing the display until the second line reads "x-tank xx.x-V" where x is the tank number and xx.x is the voltage of the battery.

b) Pressing the key 50 to "zero" advances the ones place on the tank number; pressing the key 50 to "span" advances the tens place on the tank number.

Pressure and specific gravity readings

Advancing the display until the second line reads "x.xx-PSI X.XXXX-SG" gives the pressure reading of the transducer (x.xx) and the specific gravity (X.XXXX).

Analog to digital converter reading

Advancing the display until the second line reads "xx.-A/D reading" gives the analog to digital conversion of the transducer signal. The converter is a 12-bit A/D, thus the range of the display will be from 0 to 4095.

Thus, the present invention is well adapted to carry out the objects and attain the ends and advantages mentioned above as well as those inherent therein. While a preferred embodiment of the invention has been described for the purpose of this disclosure, changes in the construction and arrangement of parts and the performance of steps can be made by those skilled in the art, which changes are encompassed within the spirit of this invention as defined by the appended claims.

What is claimed is:

1. A method of monitoring fluid in a container, comprising:
(a) sensing with a totally submersible pressure sensor the pressure of the fluid at a first depth of the fluid;
(b) sensing with the pressure sensor the pressure of the fluid at a second depth of the fluid, the second depth a known distance from the first depth;
(c) sensing with the pressure sensor the pressure of the fluid at the bottom of the fluid;
(d) determining the density of the fluid in response to the pressures sensed in said steps (a) and (b); and
(e) determining the height of the surface of the fluid in the container in response to the pressure sensed in said step (c) and the density determined in said step (d).

2. A method as defined in claim 1, wherein said step (d) includes dividing the difference between the pressures sensed in said steps (a) and (b) by the known distance to provide a quotient, and said step (e) includes Bottom Rear; Halco Flat Bottom 500 BBL; Halco DBL Comp Flat Bottom Front; Halco DBL Comp Flat Bottom Rear; Haltank 75; Haltank 160; Haltank 345; Haltank 549; Sem Corp V-Bottom 500 BBL; Trailmaster Eliptical Bottom 500 BBL; and V.E. Enterprises V-Bottom 500 BBL.

A particular aspect of the preferred embodiment system is that it operates in a master-slave mode. If the operator interface apparatus 4 are the slave devices. Thus, each fluid monitoring apparatus 4 will transmit its information only when it is polled by the master operator interface device 6. To avoid communication confusion, only one operator interface device 6 should be active (transmitter on) in the system at any one time.

When the ARC-compatible preferred embodiment operator interface device 6 is first powered up, its screen's appearance is very similar to ARC operator interface panels (OIPs). There are two major differences:

(1) there will be no unit controller truck number to select since the operator interface device 6 itself will function as a controller in the present system; and (2) the message "WAIT . . . CHECKING RF SIGNALS" will be present for no more than 20 seconds after power up in order for the operator interface device 6 to determine if there are any other operator interface devices 6 on and transmitting. This is a safeguard against multiple operator interface devices 6 acting as masters. However, the operator should make sure that there is only one master operator interface device 6 transmitting at one time.

FIG. 9 shows the Display Select Menu which lists various other screens that can be displayed through the display 28 of the preferred embodiment operator interface device 6. The various screens can be displayed by pressing and holding the display button 26c (FIG. 2) and pressing the desired letter key corresponding to the letter shown on the left of the list in FIG. 9.

FIG. 10 shows the Display Select Menu for the various screens after the fluid monitoring apparatus 4 for some tanks have become active (tanks numbered 1-4 in this example). Notice the difference between this screen and that of FIG. 9. A tank level selection has been added (selection A). Note also that the tank numbers of the active tanks are listed in numerical order at the right (1, 2, 3, 4). Thus this screen separates the active and inactive tanks via a separate tank level column. The operator can distinguish between which selection will display the status of active tanks and those of the inactive tanks.

If the Tank Level screen is desired, press either the main display key 26c (FIG. 2) or if there are more than one tank level selection, press and hold the display key 26c and the selection letter. (In the example, pressing the display key 26c and the "A" key of alphanumeric keys 22 will display the Tank Level screen and pressing the display key 26c and the "B" key will display the Tank Status screen of the active tanks.)

FIG. 11 shows the Tank Level screen. This screen can be called only if the fluid monitoring device 4 for the respective tank has answered the operator interface device 6 or if the operator has entered (defined) a tank type, fluid type, or additive concentration.

Key features of the Tank Level screen are:

1) VOLUME—the volume of fluid remaining in a particular tank based on its defined tank type.

2) STATUS—the condition of the communication between the operator interface device 6 and the fluid monitoring device 4 for the corresponding tank.

3) BAR GRAPH—graphical indication of the amount of fluid left in a tank. The bar will update each time a data message has been received from the fluid monitoring device 4 for the corresponding tank.

4) VOLUME REMAINING ON LOCATION—the total volume of all active tanks.

5) VOLUME IN TANKS DISPLAYED—the volume of the tanks shown on this screen.

FIG. 12 shows the Tank Status of the tanks that have become active (in this example, tanks numbered 1-4). Key features of the displayed information include:

1) POLL TIMER—when this timer counts down to zero, the operator interface device 6 will transmit a radio message to the corresponding fluid monitoring device 4. The fluid monitoring device 4 will then answer back in about a half second. When the operator interface device 6 transmits a message, the MSGS SENT counter will increment by one. When the operator interface device 6 receives a message from a fluid monitoring device 4, the MSGS RCVD counter will increment by one. If the operator interface device 6 transmits a message, it expects a message in return. If the operator interface device 6 does not get a message back when it expects it, it will signal a fault condition and retry the transmission up to three (3) times. The number of counts that the poll timer counts down from is a function of the rate of change of the level in the tank. If the tank level is constantly changing, then the poll timer will have a very short count (5 seconds is the shortest extreme). If the tank level is not changing very much, then the poll timer will gradually have longer counts. If the tank level stays constant long enough, the operator interface device 6 will eventually put the respective fluid monitoring device 4 in sleep mode for at most four minutes and 15 seconds. Once a device 4 is in sleep mode, it will not transmit level information until it is awake.

2) TANK TYPE—this tells both the operator interface device 6 and the fluid monitoring device 4 which type of tank is being used so that appropriate selections are made from the memory 74 in the fluid monitoring device 4 to determine the tank volume given a calculated level of fluid. The tank type is entered by the operator. The cursor key 26d and the directional arrow keys 24 (FIG. 2) can be used to go from field to field. Once the cursor is on the tank type field, the scroll list key 26a (FIG. 2) can be held down and the up and down arrow keys of the keys 24 can be used to scroll through the various tank types. With the scroll list key 26a still pressed, the enter key 26f (FIG. 2) can be used to make the selection. Once the selection is made, the operator interface device 6 will transmit the tank type information to the fluid monitoring device 4 for the respective tank on the next poll timer expiration.

3) FLUID TYPE, ADD CONC—these fields are used primarily to display information about the tank and its contents. They serve no operational purpose at the present time and can be left undefined if the operator wishes.

4) BATT STATUS—this is the status of the rechargeable battery inside the fluid monitoring devices 4. It should be at approximately 12 volts for proper operation.

5) SPEC GRAV—this field will be updated only if the tank was calibrated (zeroed and spanned across the dividing the pressure sensed in said step (c) by the quotient.

3. A method as defined in claim 1, further comprising determining the volume of fluid in the container in response to the determined height, including retaining in a memory, located with the pressure sensor, conversion tables correlating volume with height for a plurality of containers, and retrieving from the memory the volume correlated with the height determined in said step (e) for the respective container.

4. A method as defined in claim 1, further comprising transmitting, to a location remote from the container, an encoded radio frequency signal representing the height determined in said step (e).

5. A method as defined in claim 4, further comprising controlling the transmission of the encoded radio frequency signal from the location remote from the container.

6. A method of determining the amount of fluid in a container, comprising:
  (a) moving a single pressure transducer to the upper surface of the fluid in the container, including suspending the single pressure transducer on an electrical cable from a reel;
  (b) recording the pressure sensed by the single pressure transducer at the upper surface of the fluid in the container, including storing a first encoded signal in a memory contained inside the reel;
  (c) lowering the single pressure transducer a predetermined distance into the fluid in the container, including unreeling an additional length of the cable from the reel;
  (d) recording the pressure sensed by the single pressure transducer at the predetermined distance in the fluid, including storing a second encoded signal in the memory contained inside the reel;
  (e) determining a density of the fluid in the container, including using a microprocessor inside the reel for computing from the first and second encoded signals the difference between the recorded pressures of steps (b) and (d) divided by the predetermined distance;
  (f) lowering the single pressure transducer to the bottom of the fluid, including unreeling the cable from the reel until the single pressure transducer is on the bottom of the container;
  (g) recording the pressure sensed by the single pressure transducer at the bottom of the. fluid, including storing a third encoded signal in the memory contained inside the reel; and
  (h) determining the height of the fluid in the container, including using the microprocessor inside the reel for computing from the third encoded signal and the density of step (e) the quotient of the recorded pressure of step (g) divided by the density of step (e).

7. A method as defined in claim 6, further comprising determining the volume of the fluid in the container, including using the microprocessor inside the reel for retrieving from a table contained in the memory inside the reel a respective encoded signal representing the volume correlated to the height of step (h) for the particular shape of the container, said table containing encoded signals correlating volumes with heights for a plurality of different shapes of containers.

8. A method as defined in claim 6, further comprising transmitting an encoded radio frequency signal representing the height determined in said step (h) to a location remote from the container.

9. A method as defined in claim 8, further comprising controlling the transmission of the encoded radio frequency signal from a location remote from the container.

10. A method as defined in claim 8, further comprising determining the volume of the fluid in the container, including using the microprocessor inside the reel for retrieving from a table contained in the memory inside the reel a respective encoded signal representing the volume correlated to the height of step (h) for the particular shape of the container, said table containing encoded signals correlating volumes with heights for a plurality of different shapes of containers.

* * * * *